United States Patent [19]

Sutton et al.

[11] Patent Number: 5,177,023

[45] Date of Patent: Jan. 5, 1993

[54] WATER-INSOLUBLE REAGENT ELEMENTS CONTAINING SAME AND METHODS OF USE

[75] Inventors: Richard C. Sutton; Susan J. Danielson, both of Rochester, N.Y.

[73] Assignee: Eastman Kodak Company, Rochester, N.Y.

[21] Appl. No.: 742,198

[22] Filed: Aug. 5, 1991

Related U.S. Application Data

[63] Continuation of Ser. No. 81,206, Aug. 3, 1987, abandoned.

[51] Int. Cl.[5] .......................................... G01N 33/546
[52] U.S. Cl. ..................... 436/533; 436/518;
436/528; 436/531; 436/532; 436/534; 435/7.9
[58] Field of Search ............... 436/518, 528, 531, 532, 436/533, 534; 435/7.9

[56] References Cited

U.S. PATENT DOCUMENTS

| | | | |
|---|---|---|---|
| 3,619,371 | 11/1971 | Crook et al. | 436/532 |
| 3,700,609 | 10/1972 | Tregear et al. | 260/2.5 R |
| 4,161,407 | 7/1979 | Campbell | 96/114 |
| 4,181,636 | 1/1980 | Fischer | 260/8 |
| 4,259,313 | 3/1981 | Frank et al. | 424/8 |
| 4,278,651 | 7/1981 | Hales | 421/1 |
| 4,283,382 | 8/1981 | Frank et al. | 424/8 |
| 4,401,765 | 8/1983 | Craig et al. | 436/533 |
| 4,415,700 | 11/1983 | Batz et al. | 524/548 |
| 4,430,436 | 2/1984 | Koyama et al. | 436/531 |
| 4,480,042 | 10/1984 | Craig et al. | 436/533 |
| 4,569,919 | 2/1986 | Toth et al. | 436/528 |
| 4,609,707 | 9/1986 | Nowinski et al. | 525/54.1 |
| 4,670,381 | 6/1987 | Frickey et al. | 435/7 |
| 4,703,018 | 10/1987 | Craig et al. | 436/528 |

OTHER PUBLICATIONS

Wisdom, G. B., *Clinical Chemistry*, vol. 22(8), pp. 1243–1255 (1976).

Research Disclosure, publication 15963, Jul. 1977.

*Primary Examiner*—Sam Rosen
*Attorney, Agent, or Firm*—J. Lanny Tucker

[57] ABSTRACT

A water-insoluble immunoreactive reagent is prepared from a polymeric particle composed of a polymer derived from at least one ethylenically unsaturated polymerizable monomer having either pendant activated 2-substituted ethylsulfonyl or vinylsulfonyl groups. The interior of the particle is substantially free of detectable tracer material. The particle is covalently attached through the pendant groups to an immunological species which is capable of participating in an immunological reaction to complex with a corresponding receptor. This immunoreactive reagent can be incorporated in elements for use in immunoassays. In addition, they can be used in various immunological methods, including agglutination, sandwich and competitive binding assays where at least one immunological species is insolubilized.

20 Claims, No Drawings

WATER-INSOLUBLE REAGENT ELEMENTS CONTAINING SAME AND METHODS OF USE

This is a continuation of application Ser. No. 081,206, filed Aug. 3, 1987, now abandoned.

Field of the Invention

The present invention relates to a water-insoluble reagent which is useful in various immunological methods. It also relates to elements containing the reagent and to immunological methods using same.

BACKGROUND OF THE INVENTION

Immunoassays, which take advantage of natural immunological reactions, have found widespread use as analytical techniques in clinical chemistry. Because of the specificity of the reactions, they are particularly advantageous in quantifying biological analytes which are present in very low concentration and cannot be adequately quantitated by chemical techniques. Such analytes (called ligands herein) include, for example, therapeutic drugs, narcotics, antibiotics, hormones, proteins, and others known in the art. Several techniques have been devised for determining very low concentrations of ligands. For instance, a ligand may be labeled by various means to make it readily detectable. In competitive binding assays, a labeled ligand analog (identified as ligand analog herein) is placed in competition with unlabeled ligand for reaction with a fixed amount of the appropriate binding material (also called a receptor). Unknown concentrations of the ligand can be determined from the measured signal of either the bound or unbound (that is, free) ligand analog.

Sensitivity is of prime importance due to the extremely low levels of ligands to be determined. While a variety of labels can be used, fluorescent or enzyme labels are generally preferred in most immunoassays due to increased sensitivity.

Immunoassays can also be classified as either heterogeneous or homogeneous. Heterogeneous competitive binding immunoassays require a separation of bound ligand analog from free ligand analog. This separation is necessary because the properties of bound and free analog are not significantly different. Homogeneous immunoassays do not require a separation step because the properties of the bound and free analogs are sufficiently different so that they can be readily differentiated.

U.S. Pat. No. 4,670,381 (issued Jun. 2, 1987 to Frickey et al) describes a multilayer analytical element which can be used for immunoassays. This element comprises a porous spreading layer in which a receptor (for example, an antibody) for the ligand to be determined is immobilized. This receptor is immobilized on a suitable carrier material, such as glass or polymeric beads or a microorganism such as *Staphylococcus aureus*. Alternatively, the beads used to form the porous spreading layer can be used to immobilize the receptor.

Biologically active polypeptides or proteins which are attached to insoluble carrier materials, such as polymeric particles, have been used in a variety of ways in immunoassays. For example, the diagnosis of pathological or other conditions in human beings and animals is often carried out using immunological principles for the detection of an immunologically reactive species, for example antibodies or an antigen, in the body fluids of the person or animal. An antigen is generally known as a foreign substance, such as a drug, hapten, toxin, lectin, glycoprotein, polysaccharide, glycolipid, polypeptide or protein which, when introduced into the body, causes the production of certain soluble proteins known as antibodies.

Other proteins, such as enzymes, have been covalently linked to various carrier materials for use in affinity chromatography, enzymatic reactions, specific binding reactions and immunoassays. Among useful carrier materials are sheep and human erythrocytes, bacterial cells, latex particles, resinous particles and finely divided diazotized amino cellulose. For example, carrier particles prepared from sparingly water-soluble monomers (such as epoxy group-containing monomers) in the absence of emulsifiers are described in U.S. Pat. No. 4,415,700 (issued Nov. 15, 1983 to Batz et al).

Carboxylated latex particles have also been used to prepare diagnostic reagents as described, for example, in U.S. Pat. No. 4,181,636 (issued Jan. 1, 1980 to Fischer). As described therein, the conventional procedure for covalently attaching an immunologically reactive species to the particles having surface carboxyl groups involves the use of a water-soluble carbodiimide in an additional activation step. While producing useful reagents, this procedure tends to activate the exposed reactive groups of the reactive species as well as the carboxyl groups. The result is intramolecular and intermolecular crosslinking or polymerization of the immunologically reactive species, and a significant portion of the species is thus impaired from complexation with a receptor molecule. Because the reactive species, for example an antibody, is usually very costly, this problem represents a serious economic loss. Further, sensitivity of the resulting reagent may be impaired. It has also been evident that carbodiimides provide a reactive intermediate for protein attachment which is unstable and must be used immediately. This can be a serious drawback to carbodiimide chemistry.

Various other reagents have been prepared with particles having reactive groups such as epoxides, aldehydes, chloromethyl groups, amine groups and diazonium salts. All of these groups have their disadvantages. For example, epoxide groups are not stable so that the particles cannot be stored for very long. Particles having aldehyde groups generally tend to agglutinate prematurely. particles with amine groups are like the carboxylated materials by requiring an additional activation step. Diazonium compounds are unstable and therefore undesirable to work with.

U.S. Pat. No. 4,283,382 (issued Aug. 11, 1981 to Frank et al) describes immunoreactive reagents having europium chelate tracer materials within the particles. Some of the reagents are prepared from polymers having reactive chloromethyl groups (see Col. 7, lines 28–32). While such materials provide some advantages, attachment of the immunological species to such polymers requires elevated temperatures, extended reaction time and acute mixing conditions. If the attachment conditions are not just right, attachment is incomplete, resulting in a reagent with poor sensitivity.

Reagents which are composed of a protein attached to a water-insoluble particle, then are very useful in a number of methods, including immunoassays, diagnostic methods and the like. It would be very useful if highly sensitive reagents could be readily prepared in an efficient manner and under conditions which are not limiting and which do not reduce sensitivity or generate other undesirable results.

SUMMARY OF THE INVENTION

The problems noted above with known reagents are overcome with a reagent consisting essentially of:
  (a) a polymeric particle composed of a polymer derived from at least one ethylenically unsaturated polymerizable monomer having either activated 2-substituted ethylsulfonyl groups or vinylsulfonyl groups,
    the interior of the particle being substantially free of detectable tracer material, and
    the particle being covalently attached through the activated 2-substituted ethylsulfonyl groups or vinylsulfonyl groups to
  (b) an immunological species which is capable of participating in an immunological reaction to complex with a corresponding receptor.

This invention also provides an element comprising an absorbent carrier material having one or more zones, and containing in one or more of those zones the reagent described above.

Further, a method for the determination of an immunoreactive ligand in an aqueous fluid comprises:
A. in the presence of an analog of the ligand, contacting a sample of the fluid with a reagent consisting essentially of:
  (a) a polymeric particle composed of a polymer derived from at least one ethylenically unsaturated polymerizable monomer having either activated 2-substituted ethylsulfonyl groups or vinylsulfonyl groups,
    the interior of said particle being substantially free of detectable tracer material, and
    said particle being covalently attached through said activated 2-substituted ethylsulfonyl groups or vinylsulfonyl groups to
  (b) an immunological species which is capable of participating in an immunological reaction with the immunoreactive ligand,
  to form an immunological complex between the immunological species and the immunoreactive ligand, and an immunological complex between the immunological species and the ligand analog, and
B. determining the amount of the immunological complex.

An agglutination method for the determination of a ligand in an aqueous liquid comprises:
A. contacting the liquid with a reagent consisting essentially of:
  (a) a polymeric particle composed of a polymer derived from at least one ethylenically unsaturated polymerizable monomer having either activated 2-substituted ethylsufonyl group or vinylsulfonyl groups,
    the interior of the particle being substantially free of detectable tracer material, and
    the particle being covalently attached through the activated 2-substituted ethylsulfonyl groups or vinylsulfonyl groups to
  (b) an immunological species which is capable of participating in an immunological reaction with the ligand,
  so as to form an agglutinated of the reaction product of the ligand and the immunological species,
B. separating the agglutinate from unagglutinated materials, and
C. determining the amount of the agglutinate.

Further, a method for the determination of a ligand in an aqueous liquid comprises:
A. contacting the liquid with a reagent consisting essentially of:
  (a) a polymeric particle composed of a polymer derived from at least one ethylenically unsaturated polymerizable monomer having either activated 2-substituted ethylsulfonyl groups or vinylsulfonyl groups,
    the interior of the particle being substantially free of detectable tracer material, and
    the particle being covalently attached through said activated 2-substituted ethylsulfonyl groups or vinylsulfonyl groups to
  (b) a first immunological species which is capable of participating in an immunological reaction with the ligand,
  so as to form an insoluble immunological complex between the immunological species and the ligand,
B. prior to, simultaneously with or subsequent to contacting step A, contacting the ligand with a second immunological species which is immunologically reactive with the ligand but which is not immunologically reactive with the first immunological species, the second species being labeled with a detectable tracer material,
  so as to form a labeled insoluble complex, and
C. determining the labeled insoluble complex.

The present invention provides highly sensitive reagents which can be used in a wide variety of immunological techniques. The polymer particles used to prepare the reagents have readily available functional groups which readily react with proteins and other biological compounds which have free reactive amine or sulfhydryl groups. The reaction between the functional groups and the proteins or biological compounds can be rapidly carried out under mild pH conditions, low temperatures, and the agglutination, desensitization and instability of known reagents are avoided. The conditions of attachment are not as critical, that is, lower temperatures, shorter times and flexible mixing conditions can be employed without sacrificing sensitivity.

These advantages are achieved in this invention by making the polymeric particles out of ethylenically unsaturated polymerized monomers that have reactive pendant activated 2-substituted ethylsulfonyl or vinylsulfonyl groups. These groups remain available for reaction after polymerization and enable efficient attachment of immunological species having reactive amine or sulfhydryl groups.

DETAILED DESCRIPTION OF THE INVENTION

The reagent of the present invention can be used in many different immunoassays wherein the analyte (that is, the ligand) is an immunologically reactive species which has specific binding affinity for the immunological species of the reagent.

The reagent has an immunological species attached to the polymer particle. This species is a component of physiological fluids, cell and tissue extracts or a chemical compound which has at least one reactive amine or sulfhydryl group and is capable of participating in an immunological reaction with a corresponding receptor compound (natural or synthetic) which is a chemical or biological compound which has a reactive site for immunological reaction with the immunological species.

By immunological species is meant either: (1) any substance which, when presented to an immunocompetent host, will result in the production of a specific antibody capable of binding with that substance, or (2) the antibody so produced, which species participates in an antigen-antibody reaction in the use thereof.

Representative immunological species include primary amines, amino acids, peptides, proteins, lipoproteins, glycoproteins, sterines, steroids, lipids, nucleic acids, hormones, vitamins, polysaccharides, glycolipids, alkaloids, organisms (bacteria, protozoa, fungi, viruses, rickettsia and the like) and components thereof, blood substances, tissue and organ antigens and other materials known to one skilled in the art (see for example, U.S. Pat. No. 4,181,636). In some instances, the immunological species is an antibody which is directed against a hapten, drug, hormone, antibiotic or antigenic material, such as a protein, polypeptide, glycoprotein, polysaccharide, glycolipid and the like. Alternatively, the immunological species can be an antigen of some type (that is, a polypeptide or proteinaceous material) which is immunologically reactive with an antibody. In still other embodiments, the immunological species is an antibody which is directed against another antibody (that is, an anti-antibody). Both monoclonal and polyclonal antibodies can be used, and they can be whole molecules or various fragments thereof, as long as they have at least one reactive amine or sulfhydryl group which can be reacted with the pendant reactive groups of the polymeric particles.

In certain embodiments, the immunological species is an enzyme attached to the polymeric particle. Enzymes which can be attached in this manner include those which have reactive amine groups which can be reacted with the active groups on the polymer particles. Representative enzymes include aspartate aminotransaminase, alanine aminotransaminase, lactate dehydrogenase, creatine, phosphokinase, gamma glutamyl transferase, alkaline acid phosphatase, and prostatic acid phosphatase. Methods of making such reagents are well known in the art.

The water-insoluble reagent of the present invention is prepared by attaching the immunological species described above to a water-insoluble polymeric particle of specific composition. These particles are prepared from the ethylenically unsaturated polymerizable monomers described below such that there are pendant (that is, free and capable of reaction) activated 2-substituted ethylsulfonyl or vinylsulfonyl groups on the surface of the particles. In some embodiments, the entire particle may be composed of the same polymer. That is, they are homogeneous. In other embodiments, however, the particles can be what are known in the art as core-shell polymer particles having a core of a first polymer and a shell of a second polymer, as described in U.S. Pat. No. 4,401,765 (issued Aug. 30, 1983 to Craig et al). In this embodiment, the composition of the core is not critical, but the shell must be composed of the monomers described herein having the requisite pendant reactive groups. In still other embodiments, the particle can be composed of a first polymer onto which is grafted a second polymer which has the requisite pendant reactive groups (see the method described in U.S. Pat. No. 3,700,609, issued Oct. 24, 1972 to Tregear et al).

The polymeric particles are generally water-insoluble latex particles having a particle size greater than about 0.01 micrometers, preferably in the range of from about 0.01 to about 5 micrometers, and more preferably from about 0.3 to about 3 micrometers.

As described above, the polymeric particles useful in the practice of this invention are composed of a polymer derived from at least one $\alpha,\beta$-ethylenically unsaturated polymerizable monomer having either pendant activated 2-substituted ethylsulfonyl or vinylsulfonyl groups. A number of representative monomers having the requisite pendant groups are known in the art, including those disclosed in U.S. Pat. Nos. 4,161,407 (issued Jul. 17, 1979 to Campbell) and 4,548,870 (issued Oct. 22, 1985 to Ogawa et al).

Specifically useful polymers are those represented by the formula:

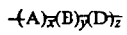

wherein A represents recurring units derived from one or more hydrophobic ethylenically unsaturated monomers. Such monomers are insoluble in water. Representative hydrophobic monomers include, but are not limited to, styrene and styrene derivatives (for example, vinyltoluene, 2,5-dimethylstyrene, 4-t-butylstyrene and 2-chlorostyrene), acrylic and methacrylic acid esters (for example, n-butyl acrylate, propyl methacrylate, methyl acrylate, ethyl methacrylate, 2-ethylhexyl methacrylate and methyl methacrylate) and vinyl acetate.

The polymer useful in this invention can be cross-linked, if desired, in any suitable fashion. One method is to incorporate a small amount, that is up to about 15 mole percent, and preferably from about 0.3 to about 5 mole percent, of a monomer having two or more ethylenically unsaturated polymerizable groups. These monomers are included among the hydrophobic monomers from which A is derived. Representative monomers are described in *Research Disclosure*, publication 19551, July, 1980, p. 304, and include for example, divinylbenzene, ethylene dimethacrylate, N,N'-methylenebisacrylamide, 2,2-dimethyl-1,3-propylene diacrylate, allyl acrylate, ethylidyne trimethacrylate and ethylene diacrylate.

Particularly useful monomers from which A is derived are styrene, vinyltoluene, ethylene dimethacrylate, butyl acrylate, divinylbenzene, 2-ethylhexyl methacrylate and methyl methacrylate.

B represents recurring units derived from one or more $\alpha,\beta$-ethylenically unsaturated monomers represented by the formula:

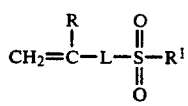

wherein R is hydrogen or substituted or unsubstituted alkyl (generally of 1 to 6 carbon atoms, such as methyl, ethyl, isopropyl or hexyl. Preferably, R is hydrogen or methyl.

$R^1$ is $-CH=CHR^2$ or $-CH_2CH_2X$ wherein X is a leaving group which is displaced by a nucleophile or is eliminated in the form of HX by treatment with a base (such as halo, acetoxy, alkylsulfonyloxy such as methylsulfonyloxy, arylsulfonyloxy such as p-tolylsulfonyloxy, trialkylammonio, for example, a trimethylammonio salt or pyridinio salt). $R^2$ is hydrogen, substituted or unsubstituted alkyl (generally of 1 to 6 carbon atoms as defined for R), or substituted or unsubstituted aryl (generally of 6 to 12 nuclear carbon atoms, such as phenyl, naphthyl, xylyl or tolyl). Preferably, $R^1$ is —$CH_2CH_2X$. This group, which is an activated 2-substituted ethyl group, can be substituted with any group which does not impair the displacement of the leaving group X.

L is a linking group which can be a substituted or unsubstituted alkylene generally having 1 to 20 carbon and hetero atoms in the backbone. This definition of alkylene is meant to include alkylene groups interrupted or terminated with oxy, thio, —$NR^3$—[wherein $R^3$ is hydrogen, substituted or unsubstituted alkyl of 1 to 6 carbon atoms (such as methyl, chloromethyl or 2-hydroxyethyl) or substituted or unsubstituted aryl of 6 to 10 carbon atoms (such as phenyl, naphthyl or xylyl]], ester (—COO—), amide (—CONH—), urylene

(—NHCNH—), sulfonyl (—$SO_2$—), carbonate, sulfonamide, azo, phosphono or other similar groups. Representative alkylene groups include methylene, ethylene, isobutylene, hexamethylene, carbonyloxyethoxycarbonyl, methylenebis(iminocarbonyl), carbonyloxydodecylenecarbonyloxyethylene, carbonyliminomethyleneiminocarbonyliminoethylene, carbonyliminomethyleneiminocarbonylethylene and other groups described or suggested by U.S. Pat. Nos. 4,161,407 and 4,548,870, noted above.

L can also be substituted or unsubstituted arylene generally having 6 to 12 nuclear carbon atoms. Representative arylene groups include phenylene, tolylene, naphthylene and others noted in the patents mentioned above. Also included in this definition of L are divalent groups which are combinations of one or more of each of the alkylene and arylene groups defined above (for example, arylenealkylene, alkylenearylenealkylene and others readily determined by one of ordinary skill in the art). Preferably, L is substituted or unsubstituted phenylenealkylene, phenylenealkylene substituted with one or more alkyl groups (as defined for R), alkoxy groups (generally of 1 to 6 carbon atoms, for example, methoxy, propoxy or butoxy) or halo groups, or carbonyliminomethyleneiminocarbonylethylene.

Representative monomers from which B can be derived include m & p-(2-chloroethylsulfonylmethyl)styrene, m & p-[2-(p-tolylsulfonyloxy)ethylsulfonylmethyl]styrene, m & p-vinylsulfonylmethylstyrene, N-[m & p-(2-chloroethylsulfonylmethyl)phenyl]acrylamide, and N-[2-(2-chloroethylsulfonyl)ethylformamidomethyl]acrylamide. The first monomer is preferred.

D represents recurring units derived from one or more ethylenically unsaturated monomers other than those represented by A or B. Generally such monomers have ionic or other hydrophilic groups which add dispersion stability to the resulting particles in aqueous solution. Useful ionic monomers include, but are not limited to, sodium 2-acrylamido-2-methylpropanesolfonate, sodium 3-acryloyloxypropanesulfonate, sodium acrylate, sodium methacrylate, and sodium styrenesulfonate, as well as other known sulfonates, sulfates, carboxylates, their salts or anhydrides, and useful nonionic polar monomers include 2-hydroxyethyl acrylate, 2,3-dihydroxypropyl acrylate, acrylamide, 2-hydroxyethyl methacrylate, N-isopropylacrylamide, 2-hydroxypropyl methacrylate, acrylonitrile and N-isobutoxymethyl acrylamide. Preferred monomers are sodium 2-acrylamido-2-methylpropanesulfonate, sodium acrylate, sodium 3-acryloyloxypropanesulfonate, sodium methacrylate, 2-hydroxyethyl acrylate, 2,3-dihydroxypropyl acrylate, acrylamide, N-isopropylacrylamide and acrylonitrile.

In the formula defined above, generally, x is from 0 to about 9.99 mole percent, y is from about 0.1 to 100 mole percent, and z is from 0 to about 20 mole percent. Preferred amounts are from about 50 to about 99.5 mole percent of x, from about 0.5 to about 50 mole percent of y and from 0 to about 10 mole percent of z.

representative polymers of which the particles are composed include:

poly[styrene-co-m & p-chloroethylsulfonylmethyl styrene] (95.5:4.5 molar ratio), and
poly{styrene-co-N-[m & p-(2-chloroethylsulfonylmethyl)phenyl]acrylamide} (99.3:0.7 molar ratio).

The first polymer is preferred. Further details relating to these polymers and representative materials can be found in U.S. Pat. Nos. 4,161,407 and 4,548,870, noted above.

The polymeric particles can be prepared using any suitable polymerization technique, including emulsion (including batch, semi-continuous and continuous) and suspension polymerization techniques, graft copolymerization, and others known to one skilled in the polymer chemistry art. Emulsion polymerization is preferred as it can be used to provide particles without the use of surfactants or emulsifiers as described for example in U.S. Pat. No. 4,415,700 (noted above) and *Research Disclosure* publication 15963 (Jul., 1977). *Research Disclosure* is a publication available from Kenneth Mason Publications, Ltd., The Old Harbourmaster's 8 North Street, Emsworth, Hampshire P010 7DD, England. Continuous emulsion polymerization is the most preferred technique, as described in the noted *Research Disclosure* publication. Other details of preparatory methods can be found in U.S. Pat. Nos. 4,161,407 and 4,548,879, noted above.

The general procedure for preparing the reagent of this invention by covalently attaching the immunological species to the particles is as follows: the polymer particles are mixed with the immunological species in an aqueous buffered solution (pH generally from about 7 to about 10) and a concentration of from about 0.01 to about 40 weight percent polymer particles (preferably from about 0.01 to about 10 weight percent). The amount of immunological species is at a ratio of species to polymer of from about 0.1:1000 to about 1:10, and preferably from about 1:100 to about 1:10. Mixing is carried out at a temperature in the range of from about 5° to about 50° C., and preferably at from about 5° to about 25° C., for from about 0.5 to about 48 hours. Any suitable buffer can be used, but a tertiary amine is preferred. The details of this procedure are illustrated in Example 1 below.

The polymeric particles used in this invention contain substantially no detectable tracer material within the particles. In the uses of this reagent, a tracer inside the particle would either be disadvantageous, unneeded where an external tracer is used, or unneeded where detecting the reagent is irrelevant to the use. A tracer is a material which is detectable using appropriate equipment and techniques. This means that the interior of the particles contain no detectable amounts of tracer materials, such as colorimetric or fluorometric dyes or compounds (such as rare earth chelates), chemiluminescent compounds, phosphorescent compounds, radioisotopes or bioluminescent compounds. In some embodiments, the reagent can have a tracer material (such as an enzyme or radioisotope) associated therewith on the particle surface or somehow attached to the immunological species. In other embodiments, the reagent has no tracer associated with it in any manner.

The reagent of the present invention can be used in the determination (qualitative or quantitative measurement) of an analyte in aqueous liquids. This determination can be made by merely determining the presence or absence of the analyte, or by quantitatively determining the amount of analyte. Where the analyte is determinable by immunological methods, it is identified as a ligand herein. In particular, the invention can be used to assay biological fluids of animals, humans or plants, but preferably of humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

The present invention can be used to detect and quantify any of a wide variety of ligands which are reactive with the immunological species on the reagent of the invention. Such ligands include, but are not limited to, proteins, hormones, drugs, haptens, carbohydrates, plant lectins or lipopolysaccharides which have one or more sites for complexing with the immunological species of the reagent. For example and preferably, the reagent comprises antibodies directed against the ligand which may be a drug or other hapten. The invention can be particularly useful in the determination of digoxin, phenytoin, phenobarbital, thyroxine, triiodothyronine, gentamicin, carbamazepine. Primidone, tobramycin or theophylline.

Alternatively, the ligand can be antibody which has two or more sites for complexation with one or more immunological species, one of which is part of the reagent of this invention. In diagnostic assays described herein, the ligand can be Streptococcus A antigen, antigens from chlamydial or gonococcal organisms, HTLV antigens or antibodies, HIV antigens or antibodies, thyroid stimulating hormone, apolipoproteins, human chorionic gonadotropin, leutinizing hormone, herpes viruses and other proteinaceous biological compounds.

The reagent can be used in a solution assay method in competitive binding immunoassays. By solution assay is meant that the reagents of this invention are used in liquid suspension in an immunoassay. Either bound (that is, complexed) or unbound (that is, uncomplexed) labeled materials can be determined. Physical separation of bound and unbound materials, if desired, can be carried out using any suitable separation technique. In using the analytical elements described below, either vertical or horizontal separation can be used.

In a competitive binding assay, the reagent is generally present in a concentration in an amount which depends upon the amount of immunological species on the polymeric particles and the type of assay conducted. It also depends upon the binding constant of the immunological species. Suitable amounts for a given assay can be readily determined by one of ordinary skill in the art. The corresponding ligand analog can be present in amounts generally known in the art for a given assay. Other materials, for example, buffers, surfactants, reagents for color formation, can be used in the assay if desired.

An assay is generally carried out by physically contacting and mixing the reagent, the labeled ligand analog and the sample to be tested in a suitable container. The resulting suspension can be incubated, if desired, to promote complexation and other reactions. The sample is then evaluated using suitable detection equipment and procedures.

In another embodiment, the reagent can be used in what are known in the art as immunometric assays, for example, "sandwich" assays. The details of such assays are provided in U.S. Pat. No. 4,486,530 (issued Dec. 4, 1984 to David et al). The reagent of the present invention is useful in such assays where the ligand to be determined has two or more epitopic sites for immunological reaction with two or more receptor molecules. The receptor molecules can be the same or different. One of the receptor molecules is identified herein as a first immunological species attached as a part of the reagent of this invention. A second immunological species is also used which is capable of immunologically reacting with the ligand at a site different than the site where the first species react. The result of the method is the formation of a ternary complex of the two distinct immunological species with the ligand. The second species (that is, the one not part of the reagent of this invention) is labeled in some manner so the resulting insoluble ternary complex can be readily detected. In a preferred immunometric assay, both immunological species are distinct antibodies directed against an antigen. They can be the same or different antibodies, whole or fragments, monoclonal or polyclonal.

In still another embodiment of this invention, the reagent of this invention is comprised of an antigen and the ligand to be determined is an antibody. A second immunological species used in the assay is a second antibody which is directed against the first antibody. The second immunological species can be labeled or unlabeled. If the second antibody is unlabeled, a labeled third antibody directed against the second antibody, or a labeled second antigen molecule reactive with the second antibody can be used.

The methods of this invention described above, can also be practiced with a dry analytical element. The simplest element can be composed of an absorbent carrier material, for example, a thin sheet of a self-supporting absorbent or bibulous material, such as filter paper or strips, which has one or more zones, at least one zone containing the reagent of this invention. Other zones can be used to contain other useful reagents. Such elements are known in the art as test strips, diagnostic elements, dip sticks or diagnostic agents.

Useful absorbent carrier materials are insoluble and maintain their structural integrity when exposed to water or biological fluids such as whole blood or serum. Useful elements can be prepared from paper, porous particulate structures, porous polymeric films, cellulose, glass fibers, woven and nonwoven fabrics (synthetic and nonsynthetic) and the like. Useful materials and procedures for making such elements are well known in the art.

Preferably, the absorbent carrier material of the dry analytical element of this invention is a porous spreading zone. This zone can be self-supporting (that is, composed of a material rigid enough to maintain its integrity), but preferably it is carried on a separate support. Such a support can be any suitable dimensionally stable, and preferably, nonporous and transparent (that is, radiation transmissive) material which transmits electromagnetic radiation of wavelength between about 200 and about 900 nm. A support of choice for a particular element should be compatible with the intended mode of detection (fluorescence, transmission or reflectance spectroscopy). Useful supports can be prepared from paper, metal foils, polystyrene, polyesters, polycarbonates or cellulose esters.

The porous spreading zone can be prepared from any suitable fibrous or non-fibrous material or mixtures of either or both. The void volume and average pore size of this zone can be varied depending upon the use intended. Useful spreading zones can be prepared using materials and procedures described, for example, in U.S. Pat. Nos. 4,292,272 (issued Sep. 29, 1981 to Kitajima et al), 3,992,158 (issued Nov. 16, 1976 to Pryzbylowicz et al), 4,258,001 (issued Mar. 24, 1981 to Pierce et al) and 4,430,436 (issued Feb. 7, 1984 to Koyama et al) and Japanese Patent Publication 57(1982)-101760.

The elements can have two or more discrete zones, either in the same layer or superimposed. At least one of the zones is preferably a porous spreading zone. The other zones can be reagent zones or registration zones as those zones are known in the art, additional spreading zones, radiation-blocking or filter zones, subbing zones or barrier zones. The zones are generally in fluid contact with each other, meaning that fluids, reagents and reaction products (for example, color dyes) can pass or be transported between superposed regions of adjacent zones. In other words, when the element is contacted with fluid, the reagents within the element become mixed and can readily interact. Preferably, each zone is a separately coated layer, although two or more zones can be separate areas in a single layer of the element. Besides the references noted above, suitable element components are described also, for example, in U.S. Pat. Nos. 4,042,335 (issued Aug. 16, 1977 to Clement), 4,132,528 (issued Jan. 2, 1979 to Eikenberry et al), and 4,144,306 (issued Mar. 13, 1979 to Figueras).

While the reagent of this invention is located in the element, it is not critical in a competitive binding assay that the ligand analog also be located therein. It is possible to add the ligand analog to the element at the time of assay. Preferably, however, the ligand analog and the reagent of this invention are both in the element, and isolated from each other in such a manner such that they will not interact prior to the assay. For example, one or both of these materials can be encapsulated with a substance that will dissolve in the applied aqueous sample. Alternatively, they can be isolated by putting them in different zones of the element where they do not mix until the assay is carried out.

In one embodiment for a competitive binding assay, an analytical element for the immunological determination of a drug or hormone, comprises a nonporous support having thereon, in order and in fluid contact, a reagent layer containing one or more reagents for providing a detectable signal in the determination, a water-soluble layer containing an enzyme-labeled analog of the drug or hormone, and a porous spreading layer containing a reagent consisting essentially of:

(a) a polymeric particle composed of a polymer represented by the formula:

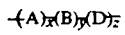

wherein A represents recurring units derived from one or more hydrophobic ethylenically unsaturated monomers, B represents recurring units derived from one or more ethylenically unsaturated monomers represented by the formula:

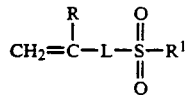

as defined above,

D represents recurring units derived from one or more ethylenically unsaturated monomers other than those represented by A or B, x is from 0 to about 99.9 mole percent, y is from about 0.1 to 100 mole percent, and z is from 0 to about 20 mole percent, the interior of the particle being substantially free of detectable tracer material, and the particle being covalently attached through the B recurring units to (b) one or more antibody molecules directed against the drug or hormone.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, analyte determination is made by taking the element from a supply roll, chip packet or other source and physically contacting it with a sample (for example, up to 500 μl) of the liquid to be tested so that the sample and reagents within the element become mixed. Such contact can be accomplished in any suitable manner, for example, by dipping or immersing the element into the sample or, preferably, by spotting the element by hand or machine with a drop of the sample with a suitable dispensing means. U.S. Pat. No. 4,670,381, noted above, provides additional details of sample application. Wash fluids can also be used, as described, for example, in U.S. Pat. No. 4,517,288 (issued May 14, 1985 to Giegel et al).

After sample application, the element can be exposed to conditioning, such as incubation, heating or the like, that may be desirable to quicken or otherwise facilitate obtaining any test result.

In still another embodiment of this invention, the reagent of this invention can be used in agglutination assays to determine the presence of a ligand which forms a complex with the immunological species in an immunological reaction. The resulting complex precipitates in a detectable agglutination or clumping of particles. The agglutination can be detected, for example, visually or with suitable light scattering detection equipment. Useful agglutination techniques are described in U.S. Pat. No. 4,419,453 (issued Dec. 6, 1983 to Dorman et al).

The following preparations illustrate representative methods of preparing polymer particles useful in the practice of this invention.

PREPARATION 1: PREPARATION OF POLY[STYRENE-CO-M & P(2-CHLOROETHYLSULFONYLMETHYL)STYRENE] (95.5:4.5 MOLAR RATIO)

Three solutions of reagents were simultaneously added and mixed using a continuous emulsion polymerization technique in a vessel at 80° C. Solution 1 contained styrene (739 g), m & p-(2-chloroethylsulfonylmethyl)styrene (82 g) and 1-dodecanethiol (8.2 g). Solution 2 contained ammonium peroxydisulfate (19.7 g) in distilled water (1152 g). Solution 3 contained sodium pyrosulfite (9.85 g) in distilled water (1152 g).

The solutions were pumped into the vessel at the following individual rates: Solution 1, 2.5 g/min., Solution 2, 2.14 g/min., and Solution 3, 2.27 g/min. After an addition time of 380 minutes, the reaction was stopped, and the yield was 1218 g at 33.4% solids. The polymer latex was then dialyzed for 3 days to yield a latex at 27.3% solids having a pH of 5. This latex was diluted to 13.5% solids for testing. Nuclear magnetic resonance analysis of the polymer indicated a molar ratio of 96:4, styrene to the sulfonyl comonomer.

PREPARATION 2: PREPARATION OF CORE/SHELL POLYMER PARTICLES HAVING A CORE OF POLY(STYRENE-CO-2-ACETOACETOXYETHYL METHACRYLATE) (85:15 MOLAR RATIO) AND A SHELL OF POLY[STYRENE-CO-M & P-(2-CHLOROETHYLSULFONYLMETHYL]STYRENE] (95.5:4.5 MOLAR RATIO)

A procedure similar to that described in Preparation 1 was followed to make a core/shell polymer. Three solutions were simultaneously added to and mixed in a vessel as follows. Solution 1 contained styrene (179.1 g), 2 acetoacetoxyethyl methacrylate (65 g) and 1-dodecanethiol (2.4 g) and was pumped at 1.5 g min. Solution 2 contained ammonium peroxydisulfate (8.14 g) in distilled water (828 g), and was pumped at 2.36 g/min. Solution 3 contained sodium pyrosulfite (4.1 g) in distilled water (828 g), and was pumped at 2.44 g/min.

The solutions were pumped into the vessel over a period of 164 minutes. The solids content was 10.3% and the residence time was 213 minutes at 80° C. The resulting polymer particles were used as the core of the resulting core/shell polymer.

The shell was provided by simultaneously adding the following solutions to the vessel containing the core particles: Solution 4 contained styrene (146.7 g), m & p-(2-chloroethylsulfonylmethyl)styrene (16.3 g) and 1-dodecanethiol (1.6 g) and was pumped at a rate of 1.41 g/min. Solutions 5 and 6 were the same as Solutions 2 and 3, respectively. The addition time for these solutions was 111 minutes at 80° C. No new particles were formed, but the monomers of Solution 4 polymerized as a copolymer shell on the core particles previously prepared. The resulting core/shell polymer solids content was 13.8% in the solution which was then dialyzed for 4 days.

The following examples illustrate the practice of the invention. In those examples, the materials used were obtained as follows:

tritiated bovine gamma globulin was prepared using the method of Tack et al, *Methods of Enzymology*, 73, pp. 138-147 (1981), Academic Press, New York using bovine gamma globulin purchased from Miles Laboratories (Naperville, Ill.), bovine serum albumin from Sigma Chemical Co. (St. Louis, Mo.), 3-{[tris(hydroxymethyl)methyl]amino} propane sulfonic acid buffer from Calbiochem (La Jolla, Calif.), and the remainder were prepared in the laboratory or obtained from Eastman Kodak Company using known starting materials and synthetic procedures.

EXAMPLE 1

Preparation of Reagent Containing Bovine Gamma Globulin

This example illustrates the preparation of a reagent of the present invention. It also demonstrates the improvement of the present invention over similar reagents prepared according to the prior art.

A portion of the latex prepared as described in Preparation 1 above containing 30 mg dry weight of polymer was combined with 0.3 mg of tritiated bovine gamma globulin protein, and the solution was brought to a final volume of 10 ml with 0.1 molar sodium borate (pH 8.5) in a centrifuge tube. Reaction of the protein with the surface reactive groups of the polymer particles was continued for 24 hours at room temperature (about 25° C.) with end-over-end rotation at 30-35 rpm while attached to a rotating plate mounted at a 45° angle. A second portion of the latex was similarly reacted with protein except that the incubation was carried out at 37° C.

A third portion of latex was similarly reacted with 1.5 g tritiated protein at 25° C., while a fourth portion was reacted with 1.5 g of protein at 37° C. In all portions of polymer, the latex particles had an average particle size of 0.68 micrometers.

Four control reagents were prepared by substituting 30 mg of a core-shell polymer having surface chloromethyl reactive groups. The core of this polymer was composed of poly(styrene-co-divinylbenzene) (99.2:0.8 molar ratio), and the shell was composed of poly(vinylbenzyl chloride-co-divinylbenzene) (98.8:1.2 molar ratio). The average particle size was about 0.68 micrometers. The core/shell polymer was divided into four portions and reacted under the same conditions with tritiated bovine gamma globulin as described for the reagent of this invention.

At the end of the described incubation times, each reaction was quenched by addition of excess bovine serum albumin (30 mg, 30 mg/ml of buffer). The reagents were then incubated another 4 hours after this addition.

The total amount of protein bound was determined by measuring: (a) the total counts per minute in a 500 microliter aliquot of the reaction mixture, (b) the counts per minute remaining in the supernatant following centrifugation of a 1 ml sample of the reaction mixture, and (c) the counts per minute from labeled protein bound to the latex following repeated washes of the pellet obtained in (b). The fraction of the labeled protein covalently bound to the particles was determined following incubation of the reacted particles in the presence of 1% sodium dodecylsulfate surfactant at 37° C. for about 24 hours with end-over-end rotation. The same procedure described above for determining the total amount of protein bound is used to determine the amount of protein covalently bound. The results are presented in Tables I and II below.

TABLE I

| Reagent (Portion) | Incubation Temperature | Tritiated Protein Used (mg) | % Protein Bound | mg Protein/ g/Polymer |
|---|---|---|---|---|
| Example 1 | | | | |
| (1) | 25° C. | 0.3 | 94 | 9.4 |
| (2) | 37° C. | 0.3 | 93 | 9.3 |
| (3) | 25° C. | 1.5 | 86 | 43 |
| (4) | 37° C. | 1.5 | 84 | 42 |
| Control | | | | |
| (1) | 25° C. | 0.3 | 94 | 9.4 |
| (2) | 37° C. | 0.3 | 90 | 9.0 |
| (3) | 25° C. | 1.5 | 69 | 34 |
| (4) | 37° C. | 1.5 | 83 | 42 |

TABLE II

| | (After Surfactant Treatment) | | | |
|---|---|---|---|---|
| Reagent (Portion) | Incubation Temperature | Tritiated Protein Used (mg) | % Protein Bound | mg Protein/ g/Polymer | Ratio Covalent/Total |
|---|---|---|---|---|---|
| Example 1 | | | | | |
| (1) | 25° C. | 0.3 | 71 | 7.1 | 0.76/1 |
| (2) | 37° C. | 0.3 | 81 | 8.1 | 0.87/1 |
| (3) | 25° C. | 1.5 | 40 | 20 | 0.46/1 |
| (4) | 37° C. | 1.5 | 46 | 23 | 0.57/1 |
| Control | | | | | |
| (1) | 25° C. | 0.3 | 46 | 4.6 | 0.43/1 |
| (2) | 37° C. | 0.3 | 75 | 7.5 | 0.77/1 |
| (3) | 25° C. | 1.5 | 19 | 9.6 | 0.20/1 |
| (4) | 37° C. | 1.5 | 52 | 26 | 0.55/1 |

This example demonstrates the preparation of a useful reagent in the practice of this invention. This reagent is labeled in the protein portion with a radioisotope. The data presented above indicate that the protein can be covalently attached to the polymeric particles containing reactive chloroethylsulfonyl groups using ambient (that is, room temperature) conditions much more efficiently than the corresponding Control materials. The chloromethyl group of the Control particles requires elevated incubation temperatures to obtain efficient (that is, high amounts of) binding. The advantage of the reagent of this invention is that lower temperatures may be required for attachment with certain immunoreactive species or enzymes which are inactivated at the higher temperatures.

It is also apparent from this example, that the reagent of this invention can be prepared without resort to activation steps or reagents as is common with some prior art procedures.

EXAMPLES 2 AND 3

Preparation and Use of Reagents in Immunoassay for Phenobarbital

This example demonstrates the preparation of two reagents of the present invention and their use in immunoassays to determine the presence of the drug, phenobarbital.

A monoclonal antibody directed against phenobarbital was prepared in the laboratory at Eastman Kodak Company using standard procedures of immunization of Balb/c mice with phenobarbital-human serum albumin. The spleens of the immunized mice were fused with myoloma cells (SP1/φ-Ag14) to generate hybridomas which produced the desired monoclonal antibodies.

In Example 2, this antibody was covalently attached to polymeric particles like those described in Example 1 above containing reactive chloroethylsulfonyl groups. In Example 3, the antibody was covalently attached to polymeric particles composed of poly[styrene-co-N-(p-chloroethylsulfonylmethylphenyl)acrylamide] (99.27:0.73 molar ratio) which had an average diameter of about 0.83 micrometers. The mass of the antibody bound to the particles was determined in a parallel experiment in which tritiated bovine gamma globulin was used in place of the anti-phenobarbital antibody. The amount of active protein bound to the particles was compared in the enzyme label binding experiment described below.

One sample of the latex particles (30 mg dry weight of polymer) was mixed with 0.3 mg of the anti-phenobarbital antibody in 10 ml of 3-{[tris(hydroxymethyl)methyl]amino}propanesulfonic acid buffer (pH 8.5, 0.1 molar). A second sample of the latex was mixed with 1.5 mg of the antibody in 10 ml of the same buffer. The attachment reactions are carried out by incubation for 24 hours with end-over-end rotation at room temperature. The reactions were stopped by the addition of bovine serum albumin (30 mg, 30 mg/ml), and the incubation was continued for another 4 hours. The reaction mixtures were then centrifuged, the supernatant discarded, and the pellets washed once with phosphate buffered saline solution (pH 7.4) and then resuspended in the saline solution.

One sample (30 mg of dry polymer) of a Control latex like that shown in Example 1 was similarly incubated with the anti-phenobarbital antibody (0.3 mg) in 10 ml of 0.1 molar sodium borate buffer at pH 8.5. A second portion of the latex was similarly incubated with 1.5 mg of the antibody in the same buffer. The attachment reactions were carried out at 37° C. instead of room temperature.

The mass of antibody bound to each latex preparation was determined by assaying the number of counts for samples run in parallel having tritiated bovine gamma globulin bound to the particles as described in Example 1. The covalent/total ratio was calculated as described in Example 1 after incubation with sodium dodecylsulfate surfactant. The relative amount of active antibody in each preparation was determined in an assay in which serial dilutions of the reagent were mixed with a fixed concentration of glucose oxidase-labeled phenobarbital ($5 \times 10^{-10}$ molar). The reagent amounts used varied from $6.3 \times 10^{-10}$ molar to $2.0 \times 10^{-7}$ molar theoretical phenobarbital binding sites based on the mass of antibody bound.

The reagent dilutions and labeled drug were incubated for about 1 hour with constant agitation at room temperature in phosphate buffered saline solution containing 1% bovine serum albumin. The amount of phenobarbital-glucose oxidase label remaining in solution following centrifugation was determined and the concentration of phenobarbital binding sites required to bind 50% of the enzyme label was determined. The results of this experiment are summarized in Tables III and IV below.

TABLE III (Mass Binding Experiment)

| Reagent | Amount Labeled Protein Used (mg) | % Bound | mg$^3$H Protein/ gm Polymer | Covalent Total |
|---|---|---|---|---|
| Example 2 | 0.3 | 88 | 8.8 | 0.86/1 |
| Example 2 | 1.5 | 62 | 31 | 0.73/1 |
| Example 3 | 0.3 | 85 | 8.5 | 0.84/1 |
| Example 3 | 1.5 | 62 | 30.8 | 0.64/1 |
| Control | 0.3 | 88 | 8.8 | 0.83/1 |
| Control | 1.5 | 73 | 37 | 0.69/1 |

TABLE IV (Latex-Enzyme Label Titration)

| Reagent | Amount Protein Used (mg) | Theoretical Phenobarbital Binding Sites to Bind 50% of Label (nmolar) |
|---|---|---|
| Example 2 | 0.3 | 43 |
| Example 2 | 1.5 | 6 |
| Example 3 | 0.3 | 13 |
| Example 3 | 1.5 | 11 |
| Control | 0.3 | 114 |
| Control | 1.5 | 25 |

This example demonstrates that the anti-phenobarbital antibody can be covalently bound to the polymeric particles having reactive chloroethylsulfonyl groups using ambient reaction conditions at very high efficiency. However, the Control reagent must be prepared at elevated temperatures in order to have efficient attachment. It also demonstrates that the antibody can be attached to form the reagent of this invention using mild conditions with a 3 to 4 times greater retention of antibody activity than for the Control reagent.

EXAMPLE 4

Preparation and Use of Reagent in Immunoassay for Digoxin

A monoclonal antibody directed against digoxin (DAS5) was purchased from Beckman.

This antibody was covalently attached to polymeric particles containing reactive chloroethylsulfonyl groups. The particles were core/shell bead particles having a core of poly(styrene-co-divinylbenzene) (99:1 molar ratio), a shell of poly[styrene-co-m- & p-(2-chloroethylsulfonylmethyl)styrene-co-divinylbenzene] (94.5:4.5:1 molar ratio), and an average diameter of about 0.65 micrometers.

One sample of the latex particles (100 mg dry weight of polymer) was mixed with 3.0 mg of the anti-digoxin antibody in 10 ml of 3-{([tris(hydroxymethyl)methyl]amino)propanesulfonic acid buffer (pH 8.5, 0.1 molar). The attachment reaction was carried out by incubation for 24 hours with end-over-end rotation at room temperature. The reaction was stopped by the addition of bovine serum albumin (100 mg, 50 mg/ml) and the incubation was continued for an additional 4 hours. The reaction mixture was centrifuged, the supernatant discarded, and the pellets washed once with phosphate buffered saline solution (pH 7.4) and then resuspended in the saline solution.

A sample of a control latex, as employed in Example 1 except having an average particle size of 0.79 μm, (100 mg of dry polymer) was similarly incubated with the anti-digoxin antibody (3 mg) in 10 ml of 0.1 molar sodium borate buffer at pH 8.5. The attachment reactions were carried out at 37° C. instead of room temperature.

The relative amount of active antibody in each preparation was determined in an assay in which serial dilutions of the reagent were mixed with a fixed concentration of horseradish peroxidase-labeled digoxin ($5 \times 10^{-11}$ molar). The reagent amounts varied from $2.5 \times 10^{-10}$ to $2.5 \times 10^{-4}$ g of beads containing the immobilized antibody.

The reagent dilutions and labeled drug were incubated for about 1 hour with constant agitation at room temperature in phosphate buffered saline containing 0.1% bovine serum albumin. The amount of digoxin-peroxidase label remaining in solution following centrifugation was determined and the concentration of beads required to bind 50% of the enzyme label was determined. The results of this experiment are summarized in Table V below:

TABLE V

| (Latex-Enzyme Label Titration) | | |
|---|---|---|
| | Amount Protein Used (mg) | Beads to Bind 50% of Label (μg) |
| Example 3 | 3 | 0.119 |
| Control | 3 | 0.562 |

This example demonstrates that the anti-digoxin antibody can be attached to form the reagent of this invention which has a five times greater retention of antibody activity than the Control reagent.

The invention has been described in detail with particular reference to preferred embodiments thereof, but it will be understood that variations and modifications can be effected within the spirit and scope of the invention.

We claim:

1. A reagent consisting essentially of:

a surfactant-free, water-insoluble polymeric latex particle composed of a vinyl addition polymer, said particle having covalently attached thereto an immunological species which is capable of participating in an immunological reaction with a corresponding receptor, said polymer being represented by the formula:

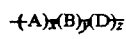

wherein A represents recurring units derived from one or more hydrophobic ethylenically unsaturated monomers, B represents recurring units derived from one or more ethylenically unsaturated monomers represented by the formula:

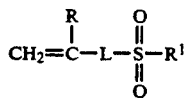

wherein R is hydrogen or substituted or unsubstituted alkyl having 1 to 6 carbon atoms, $R^1$ is $-CH=CHR^2$ or $-CH_2CH_2X$ wherein X is a leaving group which is displaced by a nucleophile or is eliminated in the form of HX by treatment with a base, and $R^2$ is hydrogen, substituted or unsubstituted alkyl having 1 to 6 carbon atoms, or substituted or unsubstituted aryl having 6 to 12 nuclear carbon atoms, and L is a linking group selected from the group consisting of substituted or unsubstituted alkylene having 1 to 20 carbon and hetero atoms, substituted or unsubstituted arylene having 6 to 12 nuclear carbon atoms, and a combination of one or more of each of said alkylene and arylene groups, D represents recurring units derived from one or more ethylenically unsaturated monomers other than those represented by A or B, x is from 0 to about 99.9 mole percent, y is from about 0.1 to 100 mole percent, and z is from 0 to about 20 mole percent, the interior of said particle being substantially free of detectable tracer material, the reagent being provided by:
(1) preparing said surfactant-free polymeric particle by emulsion polymerization of monomers A, B and C in the absence of a surfactant or emulsifier, and
(2) covalently attaching said surfactant-free polymeric particle through the reactive

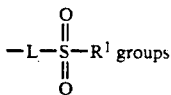

groups of the B recurring units to said immunological species.

2. The reagent of claim 1 wherein said immunological species is an enzyme, drug, antibiotic or antibody.

3. The reagent of claim 1 wherein x is from about about 50 to about 99.5 mole percent, y is from about 0.5 to about 50 mole percent, and z is from 0 to about 10 mole percent in the defined polymer.

4. The reagent of claim 1 wherein said B recurring units are derived from the defined monomers wherein R is hydrogen or methyl, $R^1$ is $-CH_2CH_2X$ and L is substituted or unsubstituted phenylenealkylene or carbonyliminometehyleneiminocarbonylethylene.

5. The reagent of claim 1 wherein said A recurring units are derived from one or more of styrene, vinyltoluene, ethylene dimethacrylate, butyl acrylate, divinylbenzene, 2-ethylhexyl methacrylate and methyl methacrylate, said B recurring units are derived from one or more of m & p-(2-chloroethylsulfonylmethyl)styrene, m & p-[2-(p-tolysulfonyloxy)ethylsulfonylmethyl]styrene, m & p-vinylsulfonylmethylstyrene, N-[m & p-(2-chloroethylsulfonylmethyl)phenyl]acrylamide, and N-[2-(2-chloroethylsulfonyl)ethylformamidomethyl]acrylamide, and said D recurring units are derived from one or more of sodium 2-acrylamido-2-methylpropanesulfonate, sodium acrylate, sodium 3-acryloyloxypropanesulfonate, sodium methacrylate, 2-hydroxyethyl acrylate, 2,3-dihydroxypropyl acrylate, acrylamide, N-isopropylacrylamide and acrylonitrile.

6. The reagent of claim 1 wherein said immunological species is an antibody selected from antibodies directed against digoxin, phenytoin, phenobarbital, thyroxine, triiodothyroniine, gentamicin, carbamazepine, Primidone, tobramycin or theophylline.

7. An element comprising an absorbent carrier material having one or more zones, and containing in one or ore of said zones a reagent as claimed in claim 1.

8. An analytical element for the immunological determination of a ligand, said element comprising a support having thereon a porous spreading zone,
said porous spreading zone containing a reagent as claimed in claim 1 wherein said immunological species is capable of participating in an immunological reaction with said ligand.

9. The element of claim 8 further comprising a labeled analog of said ligand analog, said ligand analog and said reagent being isolated from each other in different zones of said element until the time of assay.

10. An analytical element for the immunological determination of a drug or hormone, said element comprising a nonporous support having thereon, in order and in fluid contact,
a reagent layer containing one or more reagents for providing a detectable signal in said determination,
a water-soluble layer containing an enzyme-labeled analog of said drug or hormone, and
a porous spreading layer containing a reagent as claimed in claim 1, said reagent comprising antibody molecules directed against said drug or hormone.

11. The element of claim 10 containing said reagent having antibodies directed against digoxin, phenytoin, phenobarbital, thyroxine, triiodothyronine, gentamicin, carbamazepine, Primidone, tobramycin or theophylline.

12. An analytical element for the immunological determination of a drug or hormone, said element comprising a nonporous support having thereon, in order and in fluid contact,
a reagent layer containing one or more reagents for providing a detectable signal in said determination,
a porous spreading layer containing a reagent as claimed in claim 1, said reagent comprising antibody molecules directed against said drug or hormone, and
a water-soluble layer containing an enzyme-labeled analog of said drug or hormone.

13. A method for the determination of an immunological ligand in an aqueous fluid, said method comprising:
A. in the presence of an analog of said ligand, contacting a sample of said fluid with a reagent as claimed in claim 1 wherein said immunological species is capable of participating in an immunological reaction with said immunological ligand,
to form an immunological complex between said immunological species and both of said immunological ligand and ligand analog, and
B. determining the amount of said immunological complex.

14. The method of claim 13 carried out using an analytical element containing said reagent.

15. The method of claim 13 wherein said ligand analog is labeled with an enzyme, and said method is carried out in the presence of reagents which will react with said enzyme to provide a detectable dye.

16. The method of claim 13 for the determination of digoxin, phenytoin, phenobarbital, thyroxine, triiodothyronine, gentamicin, carbamazepine, Primidone, tobramycin or theophylline.

17. An agglutination method for the determination of a ligand in an aqueous liquid comprising:
A. contacting said liquid with a reagent as claimed in claim 1 wherein said immunological species is capable of participating in an immunological reaction with said ligand, so as to form an agglutinate of the reaction product of said ligand and said immunological species, B. separating said agglutinate from unagglutinated materials, and C. determining the amount of said agglutinate.

18. A method for the determination of a ligand in an aqueous liquid comprising:

A. contacting said liquid with a reagent as claimed in claim 1 comprising a first immunological species which is capable of participating in an immunological reaction with said ligand, so as to form a water-insoluble immunological complex between said immunological species and said ligand, B. prior to, simultaneously with, or subsequent to said contacting step A, contacting said ligand with a second immunological species which is immunologically reactive with said ligand but which is not immunologically reactive with said first immunological species, said second species being labeled with a detectable tracer material, so as to form a labeled insoluble complex, and C. determining the amount of said labeled water-insoluble complex.

19. The method of claim 18 wherein said ligand is an antigen and said first and second immunological species are distinct antibodies against said antigen.

20. The method of claim 18 wherein said ligand is an antibody, said first immunological species is an antigenic material reactive with said ligand, and said second immunological species is an antibody directed against said ligand.

* * * * *